(12) United States Patent
Boutaud (10) Patent No.: US 9,564,749 B2
(45) Date of Patent: Feb. 7, 2017

(54) ELECTRICAL FEEDTHROUGH FOR HOUSING OF ACTIVE IMPLANTABLE MEDICAL DEVICE

(71) Applicant: SORIN CRM SAS, Clamart (FR)

(72) Inventor: Bertrand Boutaud, Paris (FR)

(73) Assignee: SORIN CRM SAS, Clamart (FR)

( * ) Notice: Subject to any disclaimer, the term of this patent is extended or adjusted under 35 U.S.C. 154(b) by 0 days.

(21) Appl. No.: 14/539,820

(22) Filed: Nov. 12, 2014

(65) Prior Publication Data

US 2015/0136475 A1    May 21, 2015

(30) Foreign Application Priority Data

Nov. 13, 2013   (FR) ..................................... 13 61056

(51) Int. Cl.
| | | |
|---|---|---|
| *H02G 15/02* | (2006.01) | |
| *A61N 1/375* | (2006.01) | |
| *H02G 1/00* | (2006.01) | |
| *H02G 15/013* | (2006.01) | |
| *A61N 1/372* | (2006.01) | |
| *H01L 23/48* | (2006.01) | |

(52) U.S. Cl.
CPC ............ *H02G 15/02* (2013.01); *A61N 1/3754* (2013.01); *H02G 1/00* (2013.01); *H02G 15/013* (2013.01); *A61N 1/3756* (2013.01); *A61N 1/37229* (2013.01); *H01L 23/48* (2013.01); *H01L 2924/0002* (2013.01); *Y10T 29/49155* (2015.01)

(58) Field of Classification Search
CPC ....................................................... H02G 15/02

USPC .......................................................... 607/62
See application file for complete search history.

(56) References Cited

U.S. PATENT DOCUMENTS

| | | | |
|---|---|---|---|
| 5,166,097 A | 11/1992 | Tanielian | |
| 5,322,816 A * | 6/1994 | Pinter .............. | H01L 21/76251 148/DIG. 135 |
| 2011/0230937 A1* | 9/2011 | Boutaud ............. | A61N 1/3754 607/62 |
| 2012/0019886 A1* | 1/2012 | Ebefors ............. | G02B 26/0841 359/221.2 |

FOREIGN PATENT DOCUMENTS

| | | |
|---|---|---|
| EP | 2 377 573 | 10/2011 |
| WO | WO-2008/067519 | 6/2008 |

* cited by examiner

*Primary Examiner* — Timothy Thompson
*Assistant Examiner* — Stanley Tso
(74) *Attorney, Agent, or Firm* — Foley & Lardner LLP (57) ABSTRACT

A housing of an active medical device includes a metal wall having at least one feedthrough for an electrical connection through the wall. In the area of the feedthrough, the housing wall includes a contour groove extending through the thickness of wall, defining a metal islet electrically and physically isolated from the rest of the wall. The housing wall further includes an electrically insulating outer layer on the outer side of the wall extending over a region in alignment with the groove and beyond either side of the groove. The insulating outer layer includes a recess formed in alignment with the islet. The wall further includes an electrically conductive outer layer formed outside of the insulating layer and extending over the region in alignment with the groove and beyond either side of the groove. The islet is mechanically supported by the insulating and conductive outer layers.

20 Claims, 4 Drawing Sheets

ELECTRICAL FEEDTHROUGH FOR HOUSING OF ACTIVE IMPLANTABLE MEDICAL DEVICE

CROSS REFERENCE TO RELATED APPLICATIONS

This application claims the benefit of and priority to French Patent Application No. 13/61056, filed Nov. 13, 2013, which is hereby incorporated by reference herein in its entirety.

BACKGROUND

The invention relates to "active implantable medical devices" as defined by the 90/395/CEE directive of Jun. 20, 1990 of the European community counsel. This definition notably includes the devices that continuously monitor the cardiac activity and deliver if necessary to the heart electrical pulses of stimulation, cardiac resynchronization, cardioversion and/or defibrillation in case of a rhythm disorder detected by the device. It also includes the neurological devices, the cochlear implants, etc., as well as the device for pH measurement or other intracorporeal parameters.

These devices include a generator consisting of a metal housing, usually made of titanium, on which a connector head is mounted. The connector is provided with housings for mechanically and electrically connecting one or more leads to the generator housing, the leads having at their distal end various electrodes of sensing, pacing and defibrillation. The connection of the connector to various electronic circuits involves the realization of several electrical feedthroughs, between connectors assembled on the upper surface of the housing (outer side), and the interior volume of the housing where these circuits are (inner side).

Besides the connection pins on the connector head, other feedthroughs can also be provided, for example to ensure a connection with a surface electrode placed on the outside of the housing, or at the sensor integrated with a lead of the device. These feedthroughs can also be found in sub-components of medical devices such as batteries and capacitors. Such a feedthrough is for example described in EP2377573 A1 (Sorin CRM SAS).

The technique described in the EP2377573 A1 document is to superficially oxidize the outer side of the titanium housing or to deposit an insulating layer (e.g. silicon dioxide) on the outer side, and, on the inner side, to dig into the wall throughout its thickness, so as to form a contour groove defining a closed area or "islet" dedicated to the electrical conduction. This islet, created in the mass of the wall of the housing, is physically and therefore electrically isolated from the rest of the body of the housing.

An electrical connection is then performed on each side of the islet by providing on each side thereof a contact pad on which for example a connection wire to a terminal of the electronic circuit, or a connection pin of the connector, is welded. The presence on the outer side of the insulating layer, which is not inground, ensures a perfect hermeticity of the feedthrough and prevents penetration of fluid inside the housing. This layer also has the advantage of being biocompatible, biostable and resistant to corrosion.

The method can also be developed without significant additional cost, in so far as it uses only proven conventional techniques. However, this technique leaves some mechanical fragility. Indeed, after excavation of the peripheral groove surrounding the islet, the latter is completely detached from the rest of the wall of the housing (which is precisely essential to ensure the electrical insulation of the feedthrough) and is only connected to this wall by the thin superficial layer that forms an oxide "membrane" or "diaphragm" whose thickness is typically 10 to 15 microns (for a wall thickness of about 300 microns).

This residual fragility, which is intrinsic to the thinness of the oxide layer, is further increased by the rather average tolerances achieved downhole during the digging of the groove. This can locally lead to the appearance of cracks or other micro-defects, precisely near the thin oxide layer which holds the islet and wherein stress biasing the structure may be concentrated, for example because of the wires or pins welded onto the central islet.

Certain proposed embodiments of the present invention provide a solution of mechanical reinforcement of this known structure to make it more robust and tolerant to the presence of micro-defects.

Another inherent drawback in the structure described above is that it only allows to passively convey (ohmic, purely resistive conduction) an electrical signal between the inside and outside of the housing. Therefore, to provide a filter (series or parallel) to the feedthrough, it is necessary to provide an external capacitive disc carried on the inner face of the feedthrough, to which the disc is mechanically and electrically connected, for example by a conductive adhesive. This is a relatively expensive step from the industrial viewpoint since it requires numerous sub-steps that can also cause reliability problems.

Certain proposed embodiments of the present invention provide various collateral advantages, including the ability to integrate into the known structure, improved according to the invention, additional functional elements, such as an RF antenna (for the purpose of RF telemetry), electrodes, sensor elements etc. Indeed, the RF antennas, for example, are currently made from a metal wire outside the housing, which is connected to the internal electronic circuitry through a dedicated feedthrough which is then overmolded in a biocompatible plastic matrix. Again, the connection and industrialization are complex and induce an overall volume significantly higher than that of devices without RF antenna.

SUMMARY

The present disclosure relates to a housing of an active medical device (or housing element) including a metal wall having an outer side and an inner side, said wall being provided with at least one electrically insulated and hermetic feedthrough for electrical connection through the wall. The housing further includes in the region of the feedthrough: on the inner side of the wall, a closed contour groove delimiting in the wall a metal islet physically and electrically isolated from the rest of the wall, said groove extending throughout the thickness of the wall; and on the outer side of the wall, an external electrically insulating layer formed above the wall and extending over a region located at least to the right of the groove and beyond either side of the groove, this external insulating layer including a recess formed to the right of the islet in the entire thickness of the insulating outer layer.

According to certain embodiments, this housing further includes, on the outer side of the wall in the region of the feedthrough, an outer electrically conductive layer formed over the insulating outer layer and extending over said region. The electrically conductive layer at least in alignment with the groove and beyond each side of the groove, the islet being mechanically supported and sealed by both conductive and insulating outer layers. The electrically conductive outer layer can be a metal layer of titanium, platinum, palladium, gold or alloys thereof. The insulating outer layer may be an oxide layer of the metal of the wall, formed on a fraction of the thickness of this wall, or an insert layer, deposited on the surface of the wall.

According to a first embodiment of the invention, the recess also extends throughout the thickness of the conductive outer layer, so as to provide in the bottom of the recess a contact pad to the islet at the outer side of the housing block in the area of the feedthrough. In this case, the conductive outer layer may extend beyond the region of the feedthrough defining on an area a first plate of a parallel filter capacitor of the feedthrough, the other plate of the capacitor being formed by the region of the wall extending opposite the first plate.

According to a second embodiment of the invention, the recess is filled with the material of the conductive outer layer, thereby electrically connecting the islet to the conductive outer layer in the region of the feedthrough. In this case, the housing may further include in the region of the feedthrough, on the inner side of the wall, an electrically insulating inner layer formed on top of the wall and extending over the region of the islet It further includes an electrically conductive inner layer formed over the inner insulating layer and extending over the region of the islet, so as to form a contact pad to the islet, inner side of the housing. The conductive inner layer thus defines a first plate of a series filter capacitor through the feedthrough, the other plate of the capacitor being formed by the region of the wall extending opposite the first plate.

On the other hand, the conductive outer layer may extend beyond the region of the feedthrough according to a predetermined pattern defining a RF antenna, a sensor electrode or a detection/stimulation electrode element.

Finally, the housing may include in the region of the feedthrough, on the outer side of the wall, a stack formed in the insulating outer layer of alternately conductive and insulating multiple additional outer layers.

According to another embodiment, a method of creating a feedthrough in a housing of an active implantable medical device is provided. The method includes providing a housing having an outer wall and an inner wall, creating an electrically insulating outer layer on the outer wall of the housing, and creating an electrically conductive outer layer on the outside of the electrically insulating outer layer. The method further includes forming a recess in at least the electrically insulating outer layer, extending through the electrically insulating outer layer to the outer wall of the housing and forming a contour groove in the inner wall of housing, extending through the width of the wall, at a location not aligned with the recess formed in the electrically insulating outer layer. The contour groove creates an islet in the wall of the housing, the islet being electrically and physically isolated from the rest of the wall. The islet is aligned with the recess formed in the electrically insulating outer layer.

According to yet another embodiment, a method of preparing a substrate for creation of a feedthrough is provided. The method includes providing a first and a second substrate, creating a first electrically insulating layer on a first side of the first substrate, and creating a second electrically insulating layer on either the second side of the first substrate or a first side of the second substrate. The method further includes welding together the first substrate and the second substrate forming a welded structure. The welded structure includes a first electrically insulating layer on the outside of the welded structure, a second electrically insulating layer between the first and the second substrate, one of the first and second substrate between the first and second electrically insulating layers forming the retained substrate, and the other of the first and second substrate forming an exposed substrate. The method further includes thinning the exposed substrate so as to form an outer conductive layer from the substrate.

DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which.

DETAILED DESCRIPTION

Figure 1:
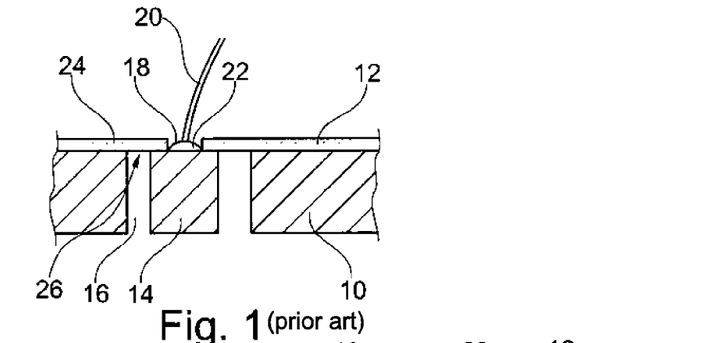
FIG. 1 is an elevation view, in section, of a feedthrough according to the prior art.

FIG. 1 shows a structure according to the prior art, such as that described in the abovementioned EP 2377573 A1. Reference 10 designates the titanium metal housing of the generator, or a separate titanium plate is a metal part which is then attached to the housing and welded thereto. An insulating layer 12 is formed above the wall 10, at least on the external face of the housing. This insulating layer 12 may be formed by oxidation of the titanium of the housing 10 on a controlled depth, or by depositing a layer of insulating material, for example silicon dioxide, on the surface of the thickness 10 of the titanium housing. The thickness of the insulating oxide layer 12 is for example of the order of 10 microns for a thickness of the housing of about 300 microns.

The structure further includes a conductor islet 14 formed in the thickness of the housing 10 by digging a groove 16. In the direction of depth, the groove 16 is recessed from the inner side of the housing in the entire thickness of the wall 10 of the metal housing. However, the insulating layer 12 is left intact, so that the islet 14 can be supported by the bridge of material formed by the insulating layer 12 between the area of the islet and the remainder of the metal layer of the housing. The outer insulating layer 12 also forms a hermetic barrier between the inside of the case and the external environment. In the plane of the surface of the housing, the groove 16 is recessed on a closed contour, so as to physically and electrically completely insulate the islet 14 from the remainder of the housing 10 around its entire periphery.

This structure also has an opening 18 formed in the outer side of the thickness of the insulating oxide layer 12 in alignment with the islet 14, so as to expose an area on which a wire 20 or a pin can be soldered to ensure electrical contact, via solder 22, with the central conductor islet 14. On the inner side, the islet 14 is connected to a connection wire to the electronic circuits enclosed in the housing of the generator 10. The connection is, for example by soldering of a connection wire (not shown), so as to produce a feedthrough insulated and sealed from the housing, from this internal connection wire to the pin or outer wire 20, at the opposite side of the housing 10. Other connection techniques may alternatively be used, such as soldering, wire bonding or contacting via a conductive elastic member.

This structure has the characteristic that the islet 14 is only connected, and mechanically supported, by the thin bridge of material 24 of the oxide layer 12. This region, particularly the bottom 26 of the groove 16, is particularly fragile. Defects or micro-cracks that weaken the bridge or "diaphragm" 24, already fragile due to its very low thickness, can appear during the process of manufacturing.

Figure 2:
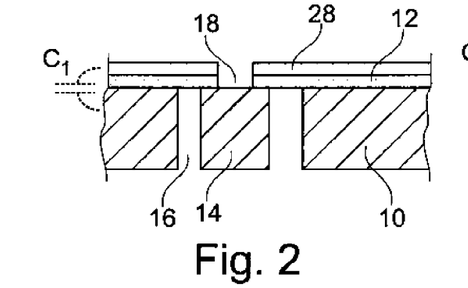
FIG. 2 is an elevation view, in section, of a feedthrough according to a first embodiment of the invention.

FIG. 2 illustrates a first embodiment according to the invention. The preferred embodiments deposit on top of the insulating outer oxide layer 12 an additional, conductive outer layer 28, e.g. by depositing a metallization of titanium or of another material such as platinum, palladium, gold and alloys thereof in a thickness of the order of several hundred nanometers to several micrometers. Titanium is preferred because of its higher affinity to the thickness of the underlying wall 10 (same expansion coefficient) and of its well-known properties of biocompatibility.

In the embodiment illustrated in FIG. 2, the conductive outer layer 28 is deposited before digging the opening 18 designed to achieve the initial contact with the conductor islet 14, which reduces handling constraints on the structure, strengthening thereof particularly during excavation of the groove 16. The method thus comprises forming the outer insulating layer 12 (deposition of an insert material or of the surface oxidation of the titanium of the wall 10) then the conductive outer layer 28 (metalizing) on the whole extent of the outer side of the wall 10. The opening 18 is formed in a subsequent step, so as to expose a contact with the central conductor islet 14 for soldering of a wire or a pin, as in the configuration illustrated in FIG. 1.

Along with the recessing of the opening to make contact 18, it is possible to etch the contours of the metallization 28 and of the insulating outer layer 12 on a predetermined surface, so as to define a structure of capacitor C1, the layers 10 and 28 forming the plates of this capacitor and the insulating oxide layer 12 forming the dielectric. If the conductive outer layer 28 is connected to the ground, an element for parallel filtering integrated to electrical feedthrough of the housing is thus obtained. The oxide insulating layer 12 is structured in the desired method, for example by photolithography.

The resulting structure allows for strengthening of the mechanical rigidity of the material bridge mechanically connecting the islet 14 to the rest of the wall of the housing 10 (due to the increase in thickness of material by adding the outer layer 28) as well as of sealing. This embodiment also provides integration of a filtering capacitive element (of a typical value in the order of 500 pF), without any mounted additional components. Furthermore, the arrangement of FIG. 2 provides the possibility of structuring the conductive outer layer 28 and the insulating outer layer 12 so as to produce elements such as a sensing electrode, a capacitive sensor element or a biochemical sensor, etc.

Figure 3:
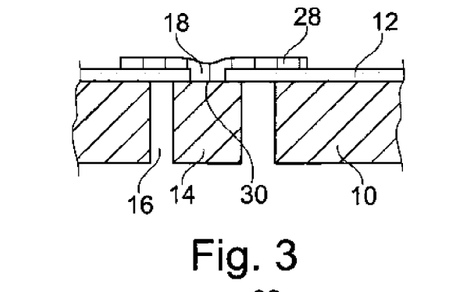
FIG. 3 is an elevation view, in section, of a feedthrough according to a second embodiment of the invention.

FIG. 3 illustrates a second embodiment of the invention. Compared to the foregoing, in this embodiment the oxide insulating layer 12 is structured, particularly to release the contact area to form the opening 18, before depositing the conductive outer layer (metallization) 28. Therefore, when the material of the conductive layer 28 is deposited during the step of metallization, the material enters the opening 18 formed in the oxide layer 12 and comes into contact 30 with the conductor islet 14, thus ensuring electrical continuity between first the islet 14 and the circuits to which it is connected inside, and then the outer conductive layer 28.

In addition to strengthening the mechanical strength and the tightness of the material bridge connecting the islet to the rest of the housing (in the same method as in the first embodiment shown in FIG. 2), this technique allows to widen the electrical connectivity with the outside, through direct contact between the outer metallization (conductive layer 28) and the central islet 14.

Figure 4:
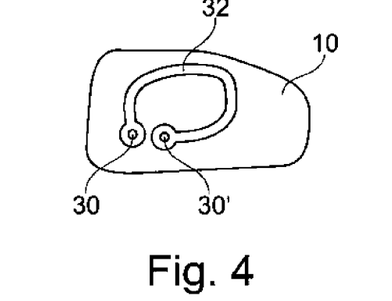
FIG. 4 is a top view showing an RF antenna integrated to the housing of the active device and realized by applying the teachings of the second embodiment of the invention.

One advantage of this embodiment is the ability to deport the external connecting elements elsewhere than at the vertical of the islet, thus avoiding mechanically stressing the fragile micro-structured area directly through a wire or a pin providing electrical contact at this very location. Another advantage is the ability to etch the conductive outer layer 28 so as to define the electronic elements to be electrically connected to the islet For example, as illustrated in FIG. 4, a loop-shaped RF antenna 32 extends in a perfectly controlled geometry between two contact points 30 and 30' to respective conductor islets, interior, connected to the electronic circuits of the generator. Such an antenna may particularly be used for wireless communication (telemetry) and/or battery charging via an inductive coupling. The technique of the invention makes it easy to give any suitable shape such as a loop, a spiral, a square, etc. or even a single straight antenna.

It is also possible to structure the conductive outer layer 28 so as to define a detection/stimulation electrode or a surface for a sensor for physico-chemical variables or physical parameters detected by resistive and/or capacitive impedance variations. The metal electrode provides a greater and independent sensing surface compared to that of titanium micromachining. On the other hand, the outer metallization may also be used for a capacitive detection, using the structure of the capacitor defined by the conductive layers 10 and 28 separated by the insulating layer 12.

Figure 5:
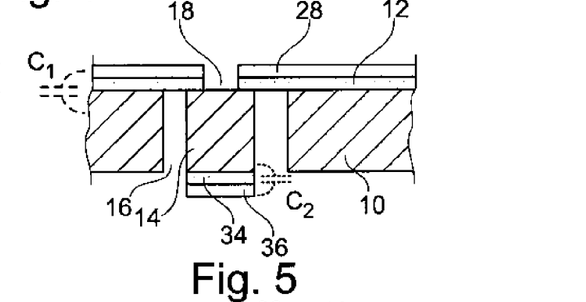
FIGS. 5 and 6 are counterparts of FIGS. 2 and 3 to illustrate an improvement wherein the feedthrough further includes a filtering series capacitor.
Figure 6:
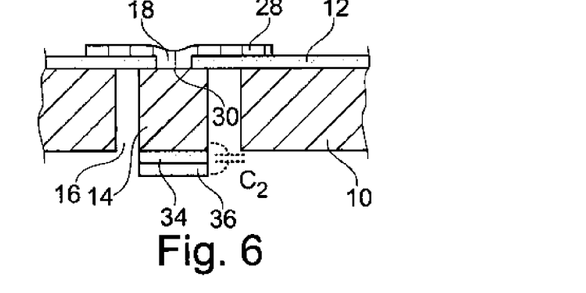

FIGS. 5 and 6 are counterparts of FIGS. 2 and 3, forming a series capacitor filter directly integrated to the feedthrough. This improvement is applicable to any of the embodiments described above. To realize this series filter, the wall 10 of the housing, on the inner side, includes an insulating layer 34 coated with a conductive layer 36. The inner layers 34, 36 are made in the same method as the corresponding outer layers 12, 28, by implementation of similar techniques, these layers 34, 36 being deposited on the inner side of the wall 10 before digging of the groove 16.

In the plane of the surface of the housing, these layers 34, 36 extend on the surface of the islet 14 and define a capacitor C2 whose armatures are formed of the titanium of the wall 10 in the region of the islet and by the inner conductive layer 36 on the one hand, and the dielectric is formed by the inner insulating layer 34, on the other hand. If the welding on the inner conductive layer 36 of a wire connecting to the internal circuits of the generator is performed, a feedthrough incorporating a series filter capacitor C2 is thus produced, without reporting any additional component, for example for the purpose of additional filtering.

Figure 7:
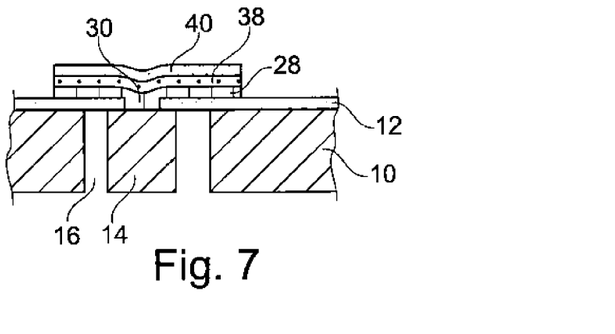
FIG. 7 illustrates an improvement of the second embodiment of the invention implementing a multi-layer structure.

FIG. 7 illustrates a further embodiment, applicable to the embodiment of FIG. 3. In this case, additional, alternately insulating or conductive, layers 38, 40, are formed on the above conductive outer layer 28 so as to define a multiple stack on the outer side of the housing. Stacking these multiple layers has the double advantage of being able to constitute an element such as a sensor or an advanced electronic function requiring several layers (e.g. a transistor); and further strengthening the structure from the mechanical and sealing point of view, the successively deposited layers increasing the thickness of the material bridge connecting the conductor islet 14 to the rest of the housing.

Figure 8:
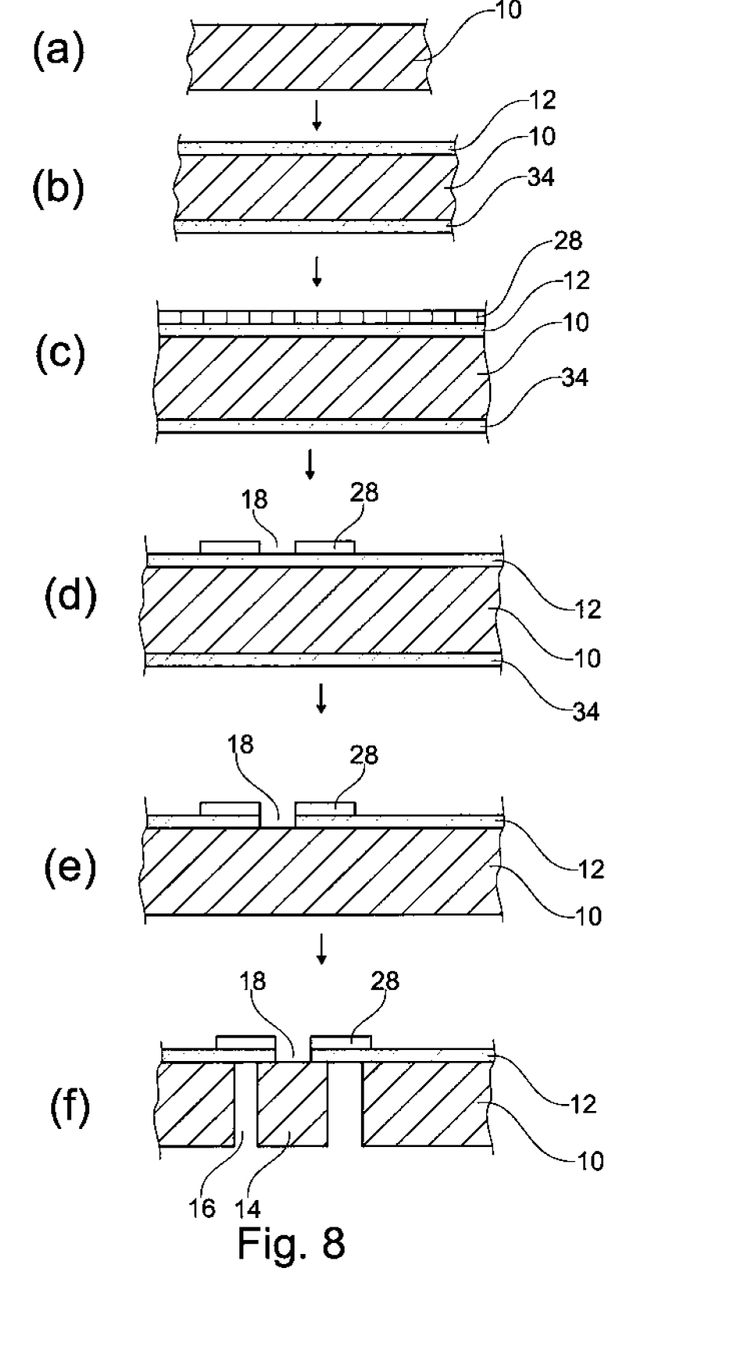
FIG. 8 shows the successive steps for producing the structure of FIG. 2 according to the first embodiment of the invention.

FIG. 8 shows the successive steps for producing the structure of FIG. 2 according to the first embodiment of the invention. The starting element is the titanium housing 10 (step a), on which insulating layers are created on both sides, with an outer insulating layer 12 and an inner insulating layer 34 (step b). These layers can be made by oxidation of the titanium housing 10 on a controlled depth, or by depositing a layer of insulating material, for example of silicon dioxide on the surface 10 of the housing thickness. The thickness of each of the layers 12, 34 is for example of the order of 10 microns to a thickness of the housing of about 300 microns.

These layers 12 and 34 may be made for example by thermal oxidation or by any other method such as plasma oxidation or chemical deposition. It is also possible to proceed by anodization, by subjecting the housing to a potential difference, and by simultaneously keeping it in contact with a solution of water and sulfuric acid, by soaking or with help of a brush-electrode.

The next step (step c) consists in forming the conductive layer 28 outer side, for example by vacuum deposition.

The next step (step d) is a step of structuring of the conductive outer layer 28, in particular to define the opening 18 that will subsequently achieve the contact, and to delimit the extent of the metal layer 28 to notably adjust the value of the series capacitor C1 (FIG. 2) associated with the feedthrough.

The next step (step e) is a step of etching the insulating outer oxide layer 12, in particular to realize the exposure of the conductive layer 10 on the outer side of the housing by the opening 18. This step may also be accompanied by an optional deletion of the insulating oxide layer 34 on the inner side of the housing.

The next step (step f) is to make the conductor islet 14 physically isolated in the thickness of the housing 10 by digging the groove 16 in the entire thickness of the housing. The widening of the groove can be made by various processes in themselves known, e.g. by chemical (interaction of species reactive with the titanium) or physical (ion bombardment) selective etching, or by any micro-structuring method, laser engraving, etc. These methods may also be combined with each other to minimize the time necessary for titanium cutting. The structure, illustrated in FIG. 2, is finally obtained after the step f.

Note also that the groove is not necessarily cylindrical. It can also have a conical shape, for example if one uses a wet etching technique that is not perfectly directional. Also note that in this implementation, the step of forming the islet (step f) is performed after the steps of deposition of the metallization (step c) and of structuring of the outer insulating oxide layer (step e). Thus, the stresses optionally suffered by the material bring no risk of weakening the final structure, to the extent that the wall of the housing 10 is still solid, because it has not yet been reduced by the digging of the groove 16.

Figure 9:
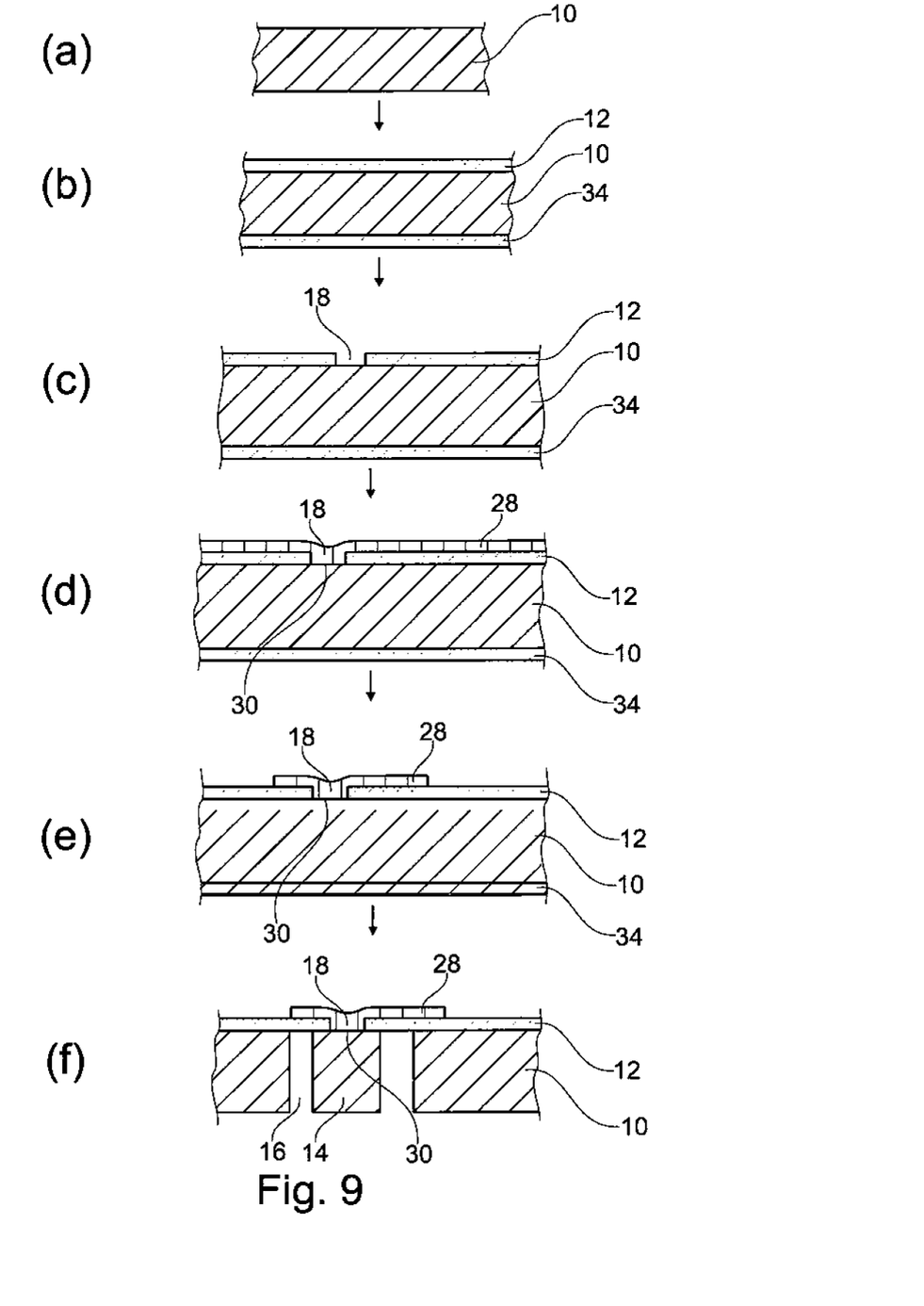
FIG. 9 shows the successive steps for producing the structure of FIG. 3 according to the second embodiment of the invention.

FIG. 9 shows the successive steps for producing the structure of FIG. 3 according to the second embodiment of the invention. The first steps a and b are identical to those of FIG. 8 of the previous embodiment.

However, the following step (step c) is a step of structuring the insulating outer oxide layer 12, using comparable techniques to those that have been mentioned in connection with step e in FIG. 7, including for forming the opening 18.

The next step (step d) is the depositing of the conductive outer layer 28 by metallization according to comparable techniques to those set forth above with respect to step c of Figure, with the only difference that this deposition occurs after structuring of the underlying oxide layer 12. This in particular allows filing the opening 18, formed in the preceding step, so as to make the direct contact catch 30 with the titanium of the wall of the housing 10.

The next step (step e) is a structuring of the conductive outer layer 28, according to comparable techniques to what has been exposed above in step d of FIG. 8. This step may be followed by an optional step of removing the oxide insulating inner layer 34 over the whole extent of the substrate.

The final step (step f) is the formation of islet 14 by digging of the groove 16 in the same method as that of the corresponding step f of FIG. 8. The final structure obtained after this step f is the one illustrated in FIG. 3.

Figure 10:
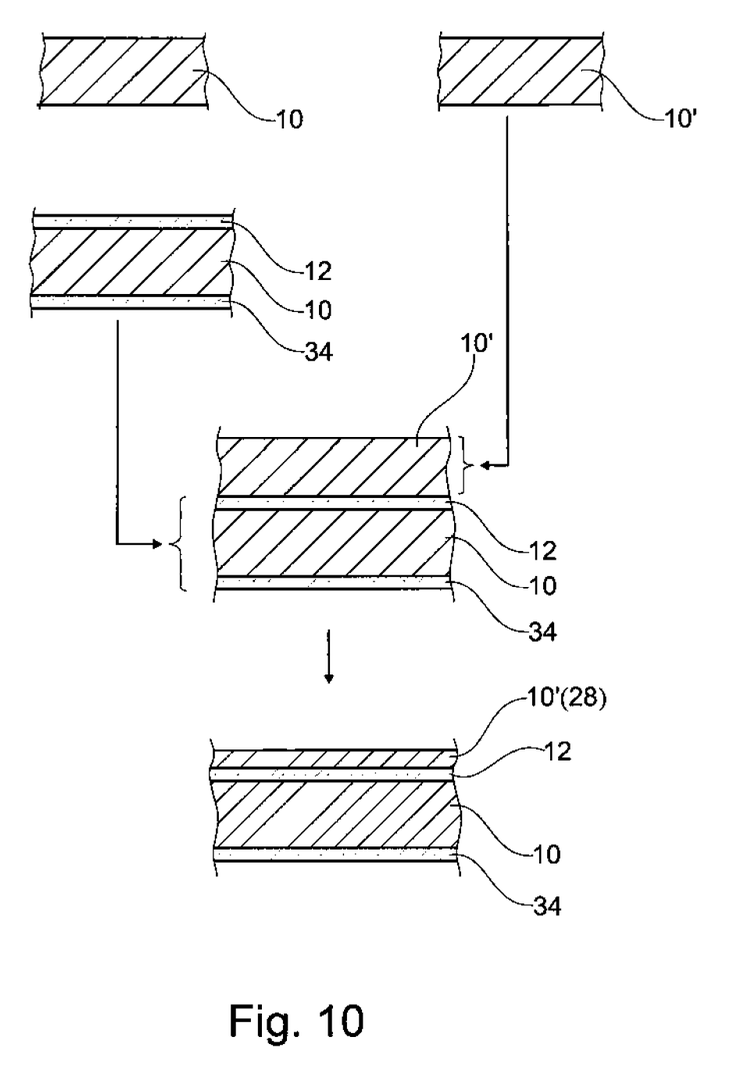
FIG. 10 illustrates an alternative preparation of the substrate for the realization of the feedthrough according to the invention.

FIG. 10 illustrates a variant for the preparation of the substrate for the realization of the feedthrough according to the invention. In this variant, instead of using a homogeneous titanium substrate on which a metallization layer is deposited, two titanium substrates 10 and 10', are separately prepared. The substrates 10 and 10' may have a substantially equal thickness (typically 300 microns), but in other embodiments may have differing thicknesses. On one of the substrates (as illustrated), or on both, an oxide layer 12, 34 is formed in the same method as the one described above for step b illustrated in FIG. 8.

The two substrates are superimposed and then welded to one another by a thermal process, thermo-compression or the like. To facilitate this welding step, an additional layer may previously be added to one or the other of the substrates 10 or 10'. At the end of this operation, a composite substrate is obtained including an oxide inner layer 12 (which originally was present on one and/or the other of the substrates 10, 10' prior to welding) and supporting an outer conductive layer, namely the thickness of the titanium substrate 10'. After thinning, the layer 10' may play the same role as the metallization 28 of the preceding embodiments, the basic structure obtained being comparable to that previously obtained at the end of step c illustrated in FIG. 8. The process continues with steps similar to what has been described above for steps d to f in FIG. 8, starting from this composite basis structure.

The invention claimed is:

1. A housing of an active medical electronic device, comprising:
   a metal wall having an outer side and an inner side, the wall being provided with at least one electrically isolated and sealed feedthrough for an electrical connection through the wall, the housing further including in an area of the feedthrough:

a contour groove, defining in the wall a metal islet electrically and physically isolated from the rest of the wall, said groove extending through a thickness of the wall;

an electrically insulating outer layer on the outer side of the wall, extending over at least a region in alignment with the groove and beyond either side of the groove, the insulating outer layer comprising a recess formed in alignment with the islet through the entire thickness of the outer insulating layer;

an electrically conductive outer layer formed outside of the insulating layer and extending over the region in alignment with the groove and beyond either side of the groove;

an electrically insulating inner layer formed on the inner side of the wall and extending over a region of the islet;

an electrically conductive inner layer formed outside of the insulating inner layer and extending over the region of the islet, forming a contact pad for contact with the islet on the inner side of the wall;

wherein the electrically conductive outer layer and the electrically conductive inner layer create a series filter capacitor; and wherein the islet is mechanically supported by the insulating and conductive outer layers.

2. The housing of claim 1, wherein the recess also extends throughout a thickness of the conductive outer layer, and wherein a contact pad is provided in a bottom of the recess in contact with the islet on an outer side of the housing in the area of the feedthrough.

3. The housing of claim 1, wherein the recess is filled with a material of the conductive outer layer, thereby electrically connecting the islet to the conductive outer layer in the area of the feedthrough.

4. The housing of claim 1, wherein the conductive outer layer extends beyond the area of the feedthrough to an area defining a first plate of a parallel filtering capacitor of the feedthrough, a second plate of the capacitor being formed by a region of the wall extending opposite the first plate.

5. The housing of claim 1,
wherein the conductive inner layer defines a first plate of a series filtering capacitor through the feedthrough, a second plate of the capacitor being formed by a region of the wall extending opposite the first plate.

6. The housing of claim 3, wherein the conductive outer layer extends beyond the area of the feedthrough according to a predetermined pattern defining at least one of a radio frequency antenna element, a sensor electrode, and a detection/stimulation electrode.

7. The housing of claim 3, wherein the housing further comprises, in the area of the feedthrough on the outer side of the wall, a stack of multiple alternating conductive and insulating outer layers.

8. The housing of claim 1, wherein the outer electrically conductive layer is a metal layer of titanium, platinum, palladium, gold or alloys thereof.

9. The housing of claim 1, wherein the insulating outer layer is a metal oxide layer of the wall, formed in a fraction of the thickness of the wall.

10. The housing of claim 1, wherein the insulating outer layer is a separate layer, deposited on a surface of the wall.

11. An active medical electronic device, comprising:
a stimulation circuit that generates a stimulation pulse;
an electrode that receives the stimulation pulse and provides stimulation to a patient; and
a housing comprising a metal wall having an outer side and an inner side, the wall being provided with at least one electrically isolated and sealed feedthrough for an electrical connection through the wall, the housing further including in an area of the feedthrough:
a contour groove, defining in the wall a metal islet electrically and physically isolated from the rest of the wall, said groove extending through a thickness of the wall;
an electrically insulating outer layer on the outer side of the wall, extending over at least a region in alignment with the groove and beyond either side of the groove, the insulating outer layer comprising a recess formed in alignment with the islet through the entire thickness of the outer insulating layer;
an electrically conductive outer layer formed outside of the insulating layer and extending over the region in alignment with the groove and beyond either side of the groove;
an electrically insulating inner layer formed on the inner side of the wall and extending over a region of the islet;
an electrically conductive inner layer formed outside of the insulating inner layer and extending over the region of the islet, forming a contact pad for contact with the islet on the inner side of the wall;
wherein the electrically conductive outer layer and the electrically conductive inner layer create a series filter capacitor; and
wherein the islet is mechanically supported by the insulating and conductive outer layers.

12. The device of claim 11, wherein the recess also extends throughout a thickness of the conductive outer layer, and wherein a contact pad is provided in a bottom of the recess in contact with the islet on an outer side of the housing in the area of the feedthrough.

13. The device of claim 11, wherein the recess is filled with a material of the conductive outer layer, thereby electrically connecting the islet to the conductive outer layer in the area of the feedthrough.

14. The device of claim 11, wherein the conductive outer layer extends beyond the area of the feedthrough to an area defining a first plate of a parallel filtering capacitor of the feedthrough, a second plate of the capacitor being formed by a region of the wall extending opposite the first plate.

15. The device of claim 11, wherein the conductive inner layer defines a first plate of a series filtering capacitor through the feedthrough, a second plate of the capacitor being formed by a region of the wall extending opposite the first plate.

16. The device of claim 11, wherein the conductive outer layer extends beyond the area of the feedthrough according to a predetermined pattern defining at least one of a radio frequency antenna element, a sensor electrode, and a detection/stimulation electrode.

17. The device of claim 11, wherein the housing further comprises, in the area of the feedthrough on the outer side of the wall, a stack of multiple alternating conductive and insulating outer layers.

18. The device of claim 11, wherein the outer electrically conductive layer is a metal layer of titanium, platinum, palladium, gold or alloys thereof.

19. The device of claim 11, wherein the insulating outer layer is a metal oxide layer of the wall, formed in a fraction of the thickness of the wall.

20. The device of claim 11, wherein the insulating outer layer is a separate layer, deposited on a surface of the wall.

* * * * *